United States Patent
Outtrup et al.

(10) Patent No.: US 6,511,371 B2
(45) Date of Patent: Jan. 28, 2003

(54) NUCLEIC ACIDS ENCODING POLYPEPTIDES HAVING PROTEOLYTIC ACTIVITY

(75) Inventors: Helle Outtrup, Værlose (DK); Søren Flensted Lassen, København (DK); Poul Erik Pedersen, Søborg (DK)

(73) Assignee: Novozymes, A/S, Bagsvaerd (DK)

( * ) Notice: Subject to any disclaimer, the term of this patent is extended or adjusted under 35 U.S.C. 154(b) by 0 days.

(21) Appl. No.: 09/966,921

(22) Filed: Sep. 28, 2001

(65) Prior Publication Data

US 2002/0103100 A1 Aug. 1, 2002

Related U.S. Application Data

(60) Provisional application No. 60/239,064, filed on Oct. 6, 2000.

(30) Foreign Application Priority Data

Oct. 2, 2000 (DK) .......................................... 2000 01455

(51) Int. Cl.[7] .......................... C12N 9/50; C12N 15/00; C12N 1/20; C07H 21/04
(52) U.S. Cl. .................. 453/219; 536/23.2; 435/320.1; 435/252.3
(58) Field of Search .............................. 435/219, 320.1, 435/252.3; 536/23.2

(56) References Cited

FOREIGN PATENT DOCUMENTS

| JP | 0204 342 A2 | * 10/1986 |
|---|---|---|
| WO | 92/17577 | 10/1992 |

OTHER PUBLICATIONS

Servant P., Production of Cry11A and Cry 11Ba Toxins in *Bacillus sphericus* Confers Toxicity towards Aedes aegypti and Resistant Culex Populations, Applied and Environmental Microbiology, 1999, 65, 3021–3026.*

Narinx E. et al. Nucleotide and Derived Amino Acid Sequence of the Subtilisin from the Antarctic Psychotroph Bacillus TA39, Biochem. Biophys. Acta, 1992, 1131, 111–113.*

* cited by examiner

*Primary Examiner*—Ponnathapuachuta Murthy
*Assistant Examiner*—Malgorzata Walicka
(74) *Attorney, Agent, or Firm*—Elias J. Lambiris

(57) ABSTRACT

The present invention relates to isolated nucleic acid sequences encoding polypeptides having proteolytic activity. The invention also relates to nucleic acid constructs, vectors, and host cells comprising the nucleic acid sequences as well as recombinant methods for producing the polypeptides.

26 Claims, 2 Drawing Sheets

NUCLEIC ACIDS ENCODING POLYPEPTIDES HAVING PROTEOLYTIC ACTIVITY

CROSS-REFERENCE TO RELATED APPLICATIONS

This application claims, under 35 U.S.C. 119, priority or the benefit of Danish application no. PA 2000 01455 filed Oct. 2, 2000 and U.S. provisional application no. 60/239,064 filed Oct. 6, 2000, the contents of which are fully incorporated herein by reference.

FIELD OF THE INVENTION

The present invention relates to isolated nucleic acid sequences encoding polypeptides having proteolytic activity. The invention also relates to nucleic acid constructs, vectors, and host cells comprising the nucleic acid sequences as well as recombinant methods for producing the polypeptides.

BACKGROUND OF THE INVENTION

In the detergent industry enzymes have for more than 30 years been implemented in washing formulations. Enzymes used in such formulations comprise proteases, lipases, amylases, cellulases, as well as other enzymes, or mixtures thereof. Commercially most important enzymes are proteases.

Detergent proteases have been developed by isolation of proteases found in nature go followed by testing in detergent formulations. Most detergent proteases are obtained from members of the genus Bacillus.

Examples of commercial protease products are Alcalase®, Esperase® and Savinase®, all supplied by Novo Nordisk A/S, Denmark. These and similar enzyme products from other commercial sources are active in detergent solutions, i.e. at pH values in the range of from 8 to 11 and in the presence of sequestering agents, surfactants and bleaching agents such as sodium borate. The Alcalase® protease is produced by strains of the species *Bacillus licheniformis*. The Esperase® and Savinase® proteases are obtained by cultivation of strains of alkalophilic Bacilli.

WO 92/17577 describes a protease isolated from Bacillus sp. TY145, NCIMB 40339. The isolated protease had a pH optimum in the range of from 8 to 11, a temperature optimum in 30 the range of from 45 to 55 C., a pI around 8.8, and an apparent molecular weight of about 38 kD. The gene producing the above-mentioned protease has now been cloned and expressed in *Bacillus subtilis*. Thus, it is an object of the present invention to provide isolated nucleic acid sequences encoding polypeptides having proteolytic activity a well as variants of said protease.

SUMMARY OF THE INVENTION

In a first aspect, the present invention relates to an isolated nucleic acid sequence encoding a polypeptide having proteolytic activity, selected from the group consisting of:
(a) a nucleic acid sequence encoding a polypeptide having an amino acid sequence which has at least 75% identity with amino acids 1 to 311 of SEQ ID NO: 2;
(b) a nucleic acid sequence having at least 70% identity with nucleotides 371 to 1303 of SEQ ID NO: 1;
(c) a nucleic acid sequence, which hybridizes under low stringency conditions with
   (i) the nucleic acid sequence of SEQ ID NO: 1,
   (ii) a subsequence of (i) of at least 100 nucleotides, or
   (iii) a complementary strand of (i) or (ii);
(d) an allelic variant of (a), (b), or (c); and
(e) a subsequence of (a), (b), (c), or (d), wherein the subsequence encodes a polypeptide fragment which has proteolytic activity.

In a second aspect, the present invention relates to a variant of the polypeptide having the amino acid sequence shown as amino acids 1 to 311 of SEQ ID NO: 1, which comprises at least one modification compared to amino acids 1 to 311 of SEQ ID NO: 1 and which has at least 75% identity with amino acids 1 to 311 of SEQ ID NO: 1.

In other aspects, the present invention also relates to detergent compositions comprising such variants, nucleic acid constructs, vectors, and host cells comprising the nucleic acid sequences as well as recombinant methods for producing the polypeptides.

DETAILED DESCRIPTION OF THE INVENTION

Figure 1:
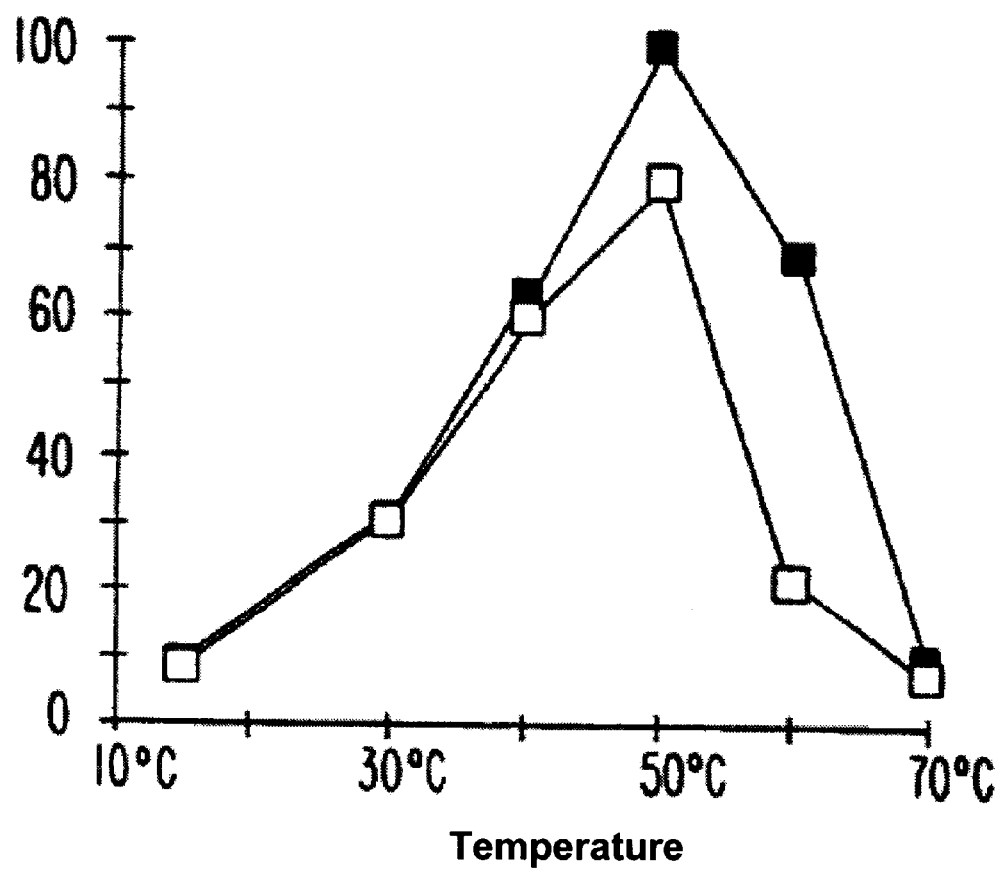
FIG. 1 shows the relation between temperature and proteolytic activity of the polypeptide having the amino acid sequence shown as amino acids 1 to 311 of SEQ ID NO: 1 (the polypeptide being obtained according to Example 1, with casein as a substrate and at pH 9.5).
Figure 2:
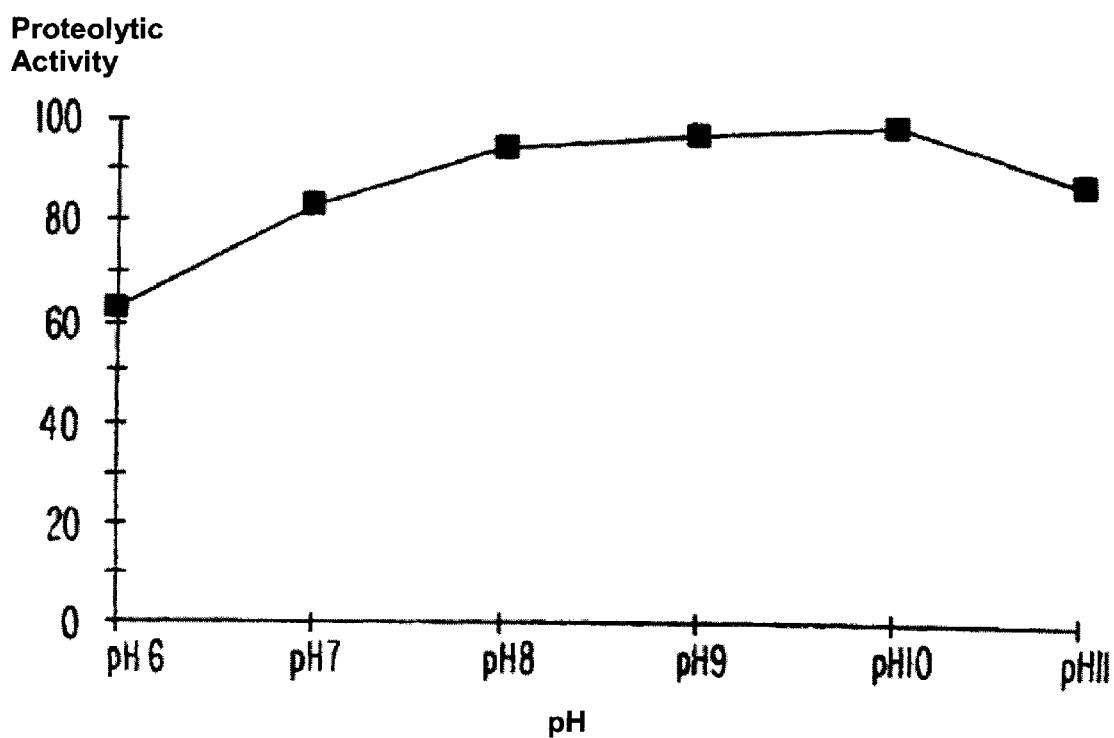
FIG. 2 shows the relation between pH and proteolytic activity of the polypeptide having the amino acid sequence shown as amino acids 1 to 311 of SEQ ID NO: 1 (the polypeptide being obtained according to Example 1, with casein as substrate and at 25° C.).

Isolated Nucleic Acid Sequences Encoding Polypeptides Having Proteolytic Activity The term "proteolytic activity" is defined herein as the capability of the polypeptide to catalyze the hydrolysis of peptide bonds. For purposes of the present invention, proteolytic activity is expressed in Casein Protease Units (CPU), where one unit CPU is defined as the amount of polypeptide liberating 1 mM of primary amine groups (determined by comparison to a serine standard) per minute under standard conditions, i.e. incubation for 30 minutes at 25° C. and pH 9.5. A folder AF 222, describing the analytical method in further details, is available upon request to Novo Nordisk A/S, which folder is hereby included by reference.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semi synthetic, synthetic origin, or any combinations thereof.

In a first embodiment, the present invention relates to isolated nucleic acid sequences encoding polypeptides having an amino acid sequence which has a degree of identity to amino acids 1 to 311 of SEQ ID NO: 2 (i.e., the mature polypeptide) of at least 75%, preferably at least 80%, more preferably at least 90%, even more preferably at least 95%, most preferably at least 97%, and even most preferably at least 99%, which have proteolytic activity (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from amino acids 1 to 311 of SEQ ID NO: 2. For purposes of the present invention, the degree of identity between two amino acid sequences is determined, e.g., by the Clustal method (Higgins, 1989, *CABIOS* 5: 151–153) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=1, gap penalty=3, windows=5, and diagonals=5.

Preferably, the nucleic acid sequence of the present invention encodes a polypeptide that comprises amino acids 1 to 311 of SEQ ID NO: 2, which is the mature polypeptide of SEQ ID NO: 2, or an allelic variant thereof; or a fragment thereof that has proteolytic activity. In another preferred embodiment, the nucleic acid sequence of the present invention encodes a polypeptide that consists of amino acids 1 to 311 of SEQ ID NO: 2 or an allelic variant thereof; or a fragment thereof that has proteolytic activity.

The present invention also encompasses nucleic acid sequences that encode a polypeptide having the amino acid sequence of SEQ ID NO: 2, which differ from SEQ ID NO: 1 by virtue of the degeneracy of the genetic code. The present invention also relates to subsequences of SEQ ID NO: 1 that encode fragments of SEQ ID NO: 2 that have proteolytic activity.

A subsequence of SEQ ID NO: 1 is a nucleic acid sequence encompassed by SEQ ID NO: 1 except that one or more nucleotides from the 5' and/or 3' end have been deleted.

A fragment of SEQ ID NO: 2 is a polypeptide having one or more amino acids deleted from the amino and/or carboxy terminus of this amino acid sequence.

An allelic variant denotes any of two or more alternative forms of a gene occupying the same chromosomal locus. Allelic variation arises naturally through mutation, and may result in go polymorphism within populations. Gene mutations can be silent (no change in the encoded polypeptide) or may encode polypeptides having altered amino acid sequences. The allelic variant of a polypeptide is a polypeptide encoded by an allelic variant of a gene.

The amino acid sequences of the homologous polypeptides may differ from the amino acid sequence of SEQ ID NO: 2 or the mature polypeptide thereof by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine, methionine and valine), aromatic amino acids (such as phenylalanine, tryptophan and tyrosine), and small amino acids (such as glycine, alanine, serine and threonine). Amino acid substitutions, which do not generally alter the specific activity, are known in the art and are described, for example, by H. Neurath and R. L. Hill, 1979, *In, The Proteins*, Academic Press, New York. The most commonly occurring exchanges are Ala/Ser, Val/lle, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/lle, Leu/Val, Ala/Glu, and Asp/Gly as well as these in reverse.

In a second embodiment, the present invention relates to isolated nucleic acid sequences which have a degree of identity to the mature polypeptide coding sequence of SEQ ID NO: 1 (i.e., nucleotides 371 to 1303) of at least 70%, preferably at least 80%, such as at least 90%, more preferably at least 95%, even more preferably at least 97%, and most preferably at least 99% identity, which encode an active polypeptide; or allelic variants and subsequences of SEQ ID NO: 1 which encode polypeptide fragments which have proteolytic activity. Preferably, the nucleic acid sequence of the present invention comprises the nucleotides 371 to 1303 of SEQ ID NO: 1. In another preferred embodiment, the nucleic acid sequence of the present invention consists of the nucleotides 371 to 1303 of SEQ ID NO: 1.

For purposes of the present invention, the degree of identity between two nucleic acid sequences is determined by, e.g., the Wilbur-Lipman method (Wilbur and Lipman, 1983, *Proceedings of the National Academy of Science USA* 80: 726–730) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=3, gap penalty=3, and windows=20.

By performing such alignments as described above, the following identities between SEQ ID NO: 1, SEQ ID NO: 2 and various known proteases were found:

Percent identity between the polypeptide having the amino acid sequence shown as amino acids 1 to 311 of SEQ ID NO: 2 and

APRSPHR[1]: 72.8%,

TA39[2]: 65.2%,

Subtilisin BPN': 33.8%,

Savinase®: 34.6%.

Percent identity between the nucleic acid sequence shown as nucleotides 371 to 1303 of SEQ ID NO: 1 and the gene encoding

APRSPHR[1]: 68.3%,

TA39[2]: 61.0%,

Subtilisin BPN': 42.4%,

Savinase®: 40.7%.

[1]P. Servant et al.: *Appl. Environ. Microbiol.* 65:3021–3026 (1999).
[2]E. Narinx et al.: *Biochim. Biophys. Acta* 1131:111–113 (1992).

In a third embodiment, the present invention relates to isolated nucleic acid sequences encoding polypeptides having proteolytic activity which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) the nucleic acid sequence of SEQ ID NO: 1, (ii) a subsequence of (i), or (iii) a complementary strand of (i) or (ii) (see: J. Sambrook, E. F. Fritsch, and T. Maniatis, 1989, *Molecular Cloning, A Laboratory Manual*, 2d edition, Cold Spring Harbor, N.Y.). The subsequence of SEQ ID NO: 1 may be at least 100 nucleotides or preferably at least 200 nucleotides. Moreover, the subsequence may encode a polypeptide fragment, which has proteolytic activity.

The nucleic acid sequence of SEQ ID NO: 1 or a subsequence thereof, as well as the amino acid sequence of SEQ ID NO: 2 or a fragment thereof, may be used to design a nucleic acid probe to identify and clone DNA encoding polypeptides having proteolytic activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$p, $^3$H, 35S, biotin, or avidin). Such probes are encompassed by the present invention.

Thus, a genomic DNA or cDNA library prepared from such other organisms may be screened for DNA that hybridizes with the probes described above and which encodes a polypeptide having proteolytic activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1 or a subsequence thereof, the carrier material is used in a Southern blot. For purposes of the present invention, hybridization indicates that the nucleic acid sequence hybridizes to a nucleic acid probe corresponding to the nucleic acid sequence shown in SEQ ID NO: 1, its complementary strand, or a subsequence thereof, under very low to very high stringency conditions. Molecules to which the nucleic acid probe hybridizes under these conditions are detected using X-ray film.

For long probes of at least 100 nucleotides in length, very low to very high stringency conditions are defined as prehybridization and hybridization at 42° C. in 5X SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1X Denhardt's solution, 1 mM sodium pyrophosphate, 1 mM sodium monobasic phosphate, 0.1 mM ATP, and 0.2 mg of yeast RNA per ml following standard Southern blotting procedures.

For short probes that are about 15 nucleotides to about 70 nucleotides in length, the carrier material is washed once in 6X SCC plus 0.1% SDS for 15 minutes and twice each for 15 minutes using 6X SSC at 5° C. to 10° C. below the calculated $T_m$.

In a fourth embodiment, the present invention relates to isolated nucleic acid sequences encoding polypeptides with proteolytic activity having the following physicochemical properties:

(a) pH optimum in the range of from pH 8 to 11 (at 25° C.), (b) temperature optimum in the range of from 45 C. to 55 C. (at pH 9.5), (c) immunochemical properties identical or partially identical to those of a protease derived from Bacillus sp. TY145, NCIMB No. 40339.

The encoded polypeptide has a temperature optimum in the range of from 45° C. to 55° C., preferably about 50° C., and a pH optimum in the range of from 8 to 11, preferably about 10.

The immunochemical properties can be determined immunologically by cross-reaction identity tests. The identity tests can be performed by the well-known Ouchterlony double immunodiffusion procedure or by tandem crossed immunoelectrophoresis according to N. H. Axelsen: *Handbook of Immunoprecipitation-in-gel Techniques*, Blackwell Scientific Publications (1983), chapters 5 and 14. The terms "antigenic identity" and "partial antigenic identity" are described in the same book, chapters 5, 19 and 20.

Monospecific antiserum was generated according to the above-mentioned method by immunizing rabbits with the purified polypeptide. The immunogen was mixed with Freund's adjuvant and injected subcutaneously into rabbits every second week. Antiserum was obtained after a total immunization period of eight weeks, and immunoglobulin was prepared therefrom as described by N. H. Axelsen, vide supra.

Ouchterlony double immunodiffusion tests showed no cross reaction between the polypeptide encoded by the nucleic acid sequence of the invention and the well-known alkaline serine proteases Alcalase®, Savinase®, Esperase®, Kazusase® and subtilisin BPN'.

The nucleic acid sequences of the present invention may be obtained from microorganisms of any genus. For purposes of the present invention, the term "obtained from" as used herein in connection with a given source shall mean that the polypeptide encoded by the nucleic acid sequence is produced by the source or by a cell in which the nucleic acid sequence from the source has been inserted.

The nucleic acid sequences may be obtained from a bacterial source. For example, these polypeptides may be obtained from a gram positive bacterium such as a Bacillus strain, e.g., *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus*

*stearothermophilus, Bacillus subtilis,* or *Bacillus thuringiensis*; or a Streptomyces strain, e.g., *Streptomyces lividans* or *Streptomyces murinus*; or from a gram negative bacterium, e.g., *E. coli* or Pseudomonas sp.

In a preferred embodiment, the nucleic acid sequences are obtained from Bacillus sp. TY145, and most preferably from Bacillus sp. TY145, NCIMB No. 40339, e.g., the nucleic acid sequence set forth in SEQ ID NO: 1.

The preferred microorganism, i.e. Bacillus sp. TY145, is described in WO 92/17577 and was deposited on Dec. 3, 1990 under the accession number NCIMB No. 40339 as mentioned right above.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the National Collections of Industrial & Marine Bacteria Ltd. (NCIMB), the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such nucleic acid sequences may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., As Sambrook et al., 1989, supra).

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of Bacillus, or another or related organism and thus, for example, may be an allelic or species variant of the polypeptide encoding region of the nucleic acid sequence.

The polypeptides encoded by the isolated nucleic acid sequences of the present invention have at least 20%, preferably at least 40%, more preferably at least 60%, even more preferably at least 80%, even more preferably at least 90%, and most preferably at least 100% of the proteolytic activity of the mature polypeptide of SEQ ID NO: 2.

Modification of a nucleic acid sequence of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variant sequence may be constructed on the basis of the nucleic acid sequence presented as the polypeptide encoding part of SEQ ID NO: 1, e.g., a subsequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95–107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, Science 244: 1081–1085). In the latter technique, mutations are introduced at every positively charged residue in the molecule, and the resultant mutant molecules are tested for proteolytic activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, *Science* 255: 306–312; Smith et al, 1992, *Journal of Molecular Biology* 224: 899–904; Wlodaver et al., 1992, *FEBS Letters* 309: 59–64).

A nucleic acid sequence of the present invention may also encode fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

Variants

In a further aspect, the present invention also relates to a variant of the polypeptide having the amino acid sequence shown as amino acids 1 to 311 of SEQ ID NO: 2, which comprises at least one modification compared to amino acids 1 to 311 of SEQ ID NO: 2 and which has at least 75% identity with amino acids I to 311 of SEQ ID NO: 2. Preferably, the number of modifications is at the most 20, e.g. at the most 15. In an interesting embodiment of the invention, the number of modifications is at the most 14, e.g. at the most 13, at the most 12, at the most 11, at the most 10, at the most 9, at the most 8, at the most 7, at the most 6, or at the most 5. In a particular interesting embodiment of the invention, the number of modifications is at the most 4, such as at the most 3, e.g. at the most 2, e.g. only one modification. Independent of the exact number of modifications, the number of modifications should be so that the variant in question still has at least 75% identity with amino acids 1 to 311 of SEQ ID NO: 2. Preferably, the variant in question has at least 80% identity, such as at least 90% identity, e.g. at least 95% identity, at least 97% identity or at least 99% identity with amino acids 1 to 311 of SEQ ID NO: 2.

When used herein, the term "variant" means a polypeptide having proteolytic activity, which has been produced by an organism, which is expressing a mutant gene as compared to SEQ ID NO: 1. The mutant gene, from which said variant is produced when expressed in a suitable host, may have been obtained by mutation of the nucleic acid sequence disclosed in SEQ ID NO: 1. Also, the mutant gene may have been prepared by the DNA shuffling technique.

In the context of the present invention the term "modification(s)" is intended to mean any chemical modification of the polypeptide having the amino acid sequence shown as amino acids 1 to 311 of SEQ ID NO: 2 as well as genetic manipulation of the DNA encoding that polypeptide. The modification(s) can be replacement(s) of the amino acid side chain(s), substitution(s), deletion(s) and/or insertions(s) in or at the amino acid(s) of interest.

Examples of modifications include, but are not limited to, amino acid changes which are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20–25 residues; or a small extension that facilitates purification by changing net charge or another function, such as a poly-histidine tract, an antigenic epitope or a binding domain.

Examples of conservative substitutions are within the group of basic amino acids (such as arginine, lysine and histidine), acidic amino acids (such as glutamic acid and aspartic acid), polar amino acids (such as glutamine and asparagine), hydrophobic amino acids (such as leucine, isoleucine, methionine and valine), aromatic amino acids (such as phenylalanine, tryptophan and tyrosine), and small amino acids (such as glycine, alanine, serine and threonine). Amino acid substitutions, which do not generally alter the specific activity, are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

The variants of the invention are useful exhibiting excellent wash performance when used in cleaning or detergent composition, in particular in liquid detergent compositions (vide infra).

Producing a Variant

Many methods for cloning a polypeptide and for introducing substitutions, deletions and insertions into genes (e.g. subtilase genes) are well known in the art.

In general standard procedures for cloning of genes and introducing insertions (random and/or site directed) into said genes may be used in order to obtain a variant according to the invention. For further description of suitable techniques reference is made to Sambrook et al. (1989) Molecular cloning: A laboratory manual, Cold Spring Harbor Lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990); and WO 96/34946.

Further, a variant according to the invention may be constructed by standard techniques for artificial creation of diversity, such as by DNA shuffling of different subtilase genes (WO 95/22625; Stemmer WPC, Nature 370:389–91 (1994)).

Nucleic Acid Constructs

The present invention also relates to nucleic acid constructs comprising a nucleic acid sequence of the present invention operably linked to one or more control sequences, which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence, which directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components that are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence that is recognized by a host cell for expression of the nucleic acid sequence. The promoter sequence contains transcriptional control sequences, which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727–3731), as well as the tac promoter (DeBoer et al., 1983, *Proceedings of the National Academy of Sciences USA* 80: 21–25). Further promoters are described in "Useful proteins from recombinant bacteria" in *Scientific American*, 1980, 242: 74–94; and in Sambrook et al., 1989, supra.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator that is functional in the host cell of choice may be used in the present invention.

The control sequence may also be a suitable leader sequence, a non-translated region of an mRNA that is important for translation by the host cell. The leader sequence is operably linked to the 5' terminus of the nucleic acid sequence encoding the polypeptide. Any leader sequence that is functional in the host cell of choice may be used in the present invention.

The control sequence may also be a polyadenylation sequence, a sequence which is operably linked to the 3' terminus of the nucleic acid sequence and which, when transcribed, is recognized by the host cell as a signal to add polyadenosine residues to transcribed mRNA. Any polyadenylation sequence, which is functional in the host cell of choice, may be used in the present invention.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region that directs the expressed polypeptide into the secretory pathway of a host cell of choice may be used in the present invention.

Effective signal peptide coding regions for bacterial host cells are the signal peptide coding regions obtained from the genes for Bacillus NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109–137.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of the polypeptide and the signal peptide region is positioned next to the amino terminus of the propeptide region.

It may also be desirable to add regulatory sequences that allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. Other examples of regulatory sequences are those that allow for gene amplification.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a mini-chromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers that permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers that confer antibiotic resistance such as ampicillin, kanamycin, chloramphenicol or tetracycline resistance.

The vectors of the present invention preferably contain an element(s) that permits stable integration of the vector into the host cell genome or autonomous replication of the vector in the cell independent of the genome of the cell.

For integration into the host cell genome, the vector may rely on the nucleic acid sequence encoding the polypeptide or any other element of the vector for stable integration of the vector into the genome by homologous or non-homologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMB1 permitting replication in Bacillus. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular cells are bacterial cells such as gram positive bacteria including, but not limited to, a Bacillus cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a Streptomyces cell, e.g., *Streptomyces lividans* or *Streptomyces murinus*, or gram negative bacteria such as *E. coli* and Pseudomonas sp. In a preferred embodiment, the bacterial host cell is a *Bacillus lentus, Bacillus licheniformis, Bacillus stearothermophilus* or *Bacillus subtilis* cell. In another preferred embodiment, the Bacillus cell is an alkalophilic Bacillus.

The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizen, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

Methods of Production

The present invention also relates to methods for producing a polypeptide comprising (a) cultivating a host cell of the invention under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fomenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, to but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Uses

The polypeptides (including the variants) having proteolytic activity encoded by the nucleic acid sequences of the present invention are useful as ingredients in detergent compositions. In addition to the polypeptides having proteolytic activity, described herein, such detergent compositions typically comprise one or more surfactants, which may be of an anionic, non-ionic, cat-ionic, amphoteric or zwitterionic type, or a mixture of these. Typical examples of anionic surfactants are linear alkyl benzene sulfonates (LAS), alkyl sulfates (AS), alpha olefin sulfonates (AOS), alcohol ethoxy sulfates (AES) and alkali metal salts of natural fatty acids. Examples of non-ionic surfactants are alkyl polyethylene glycol ethers, nonylphenol polyethylene glycol ethers, fatty acids esters of sucrose and glucose, and esters of polyethoxylated alkyl glucoside.

The detergent composition may also contain other detergent ingredients known in the art such as builders, bleaching agents, bleach activators, anti-corrosion agents, sequestering agents, anti soil-redeposition agents, perfumes, stabilizers for the enzymes and bleaching agents, formulations aids, optical brighteners, foam boosters, chelating agents, fillers, fabric softeners, etc. The detergent composition may be formulated substantially as described in J. Falbe: *Surfactants in Consumer Products. Theory, Technology and Application*; Springer Verlag 1987, in particular the section entitled "Frame formulations for liquid/powder heavy-duty detergents".

It is at present contemplated that the detergent composition may contain the enzyme preparation in an amount corresponding to 0.0005–0.5 CPU of the proteolytic enzyme per liter of washing liquor.

The detergent compositions can be formulated in any convenient form, such as powders, liquids, etc.

The detergent composition of the invention may advantageously include one or more other enzymes, e.g. lipases, amylases, cellulases, oxidases, peroxidases and/or other proteases, conventionally included in detergent compositions.

The polypeptide having proteolytic activity may be included in a detergent composition by adding separate additives containing the detergent protease, or by adding a combined additive comprising different detergent enzymes.

The additive of the invention can be formulated e.g. as granulates, liquids, slurries, etc. Preferred detergent additive formulations are non-dusting granulates, liquids, in particular stabilized liquids, slurries, or protected enzymes. Dust free granulates may be produced e.g. according to GB Patent Publication No. 1,362,365 or U.S. Pat. No. 4,106,991, and may optionally be coated by methods known in the art. The detergent enzymes may be mixed before or after granulation. Liquid enzyme preparations may, for instance, be stabilized by adding a polyol such as e.g. propylene glycol, a sugar or sugar alcohol, lactic acid or boric acid, according to established methods. Other enzyme stabilizers are well known in the art. Protected enzymes may be prepared according to the method disclosed in EP Patent Publication No. 238,216.

The present invention is further described by the following examples, which should not be construed as limiting the scope of the invention.

EXAMPLES

GENERAL MOLECULAR BIOLOGY METHODS

Unless otherwise mentioned the DNA manipulations and transformations were performed using standard methods of molecular biology (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for Bacillus". John Wiley and Sons, 1990). Enzymes for DNA manipulations were used according to the specifications of the suppliers.

Unless otherwise mentioned all enzymes for DNA manipulations, such as e.g. restriction endonucleases, ligases etc., are obtained from New England Biolabs, Inc.

Chemicals used as buffers and substrates were commercial products of at least reagent grade.

Example 1

Cultivation of Bacillus sp. TY145

Bacillus sp. TY145 was cultivated at 25° C. on a rotary shaking table (300 r.p.m.) in 500 ml baffled Erlenmeyer flasks containing 100 ml of medium of the following composition (per liter):

Potato starch 100 g
Ground barley 50 g
Soybean flour 20 g
$Na_2HPO_4 \times 12\ H_2O$ 9 g
Pluronic® 0.1 g
Sodium caseinate 10 g The starch in the medium is liquefied with α-amylase and the medium is sterilized by heating at 120° C. for 45 minutes.

After sterilization the pH of the medium is adjusted to 9.0 by addition of 10 ml of a 1 M solution of sodium bicarbonate.

After 5 days of incubation the proteolytic activity of the culture was determined using the method described herein. After cultivation, the enzyme activity of the broth was 10 CPU/l.

After separation of the solid material the protease was purified by a conventional chromatographic method.

Yield from 1 liter of culture broth was 50 ml with 57 CPU/l. Purity was more than 90% as judged by SDS-PAGE.

Example 2

Wash Performance

The wash performance tests were performed on grass soiling on cotton, in a model wash system at 20° C., isothermically for 10 minutes.

2.0 g/l of a commercial American type liquid detergent was used in the tests. The detergent did not contain any enzymes prior to the addition of the protease of the invention. The detergent was dissolved in approx. 6°dH (German Hardness) water, and the pH was measured to approx. 8. The textile/wash liquor ratio was approximately 6 g textile per liter of detergent solution. The enzyme preparation according to Example 1 was used at enzyme protein concentrations of 0.01; 0.04; 0.08; 0.16, and 0.5 CPU/liter.

Subsequent to washing, the fabric was rinsed in running tap water for 25 minutes and air-dried. The wash performance was determined by the change ($\Delta R$) of the remission (%R) at 460 nm measured on a Datacolor Elrephometer 2000, $\Delta R$ being the remission after wash with the polypeptide having the amino acid sequence shown as amino acids 1 to 311 of SEQ ID NO: 2 minus the remission after wash with no protease added.

The test results are shown in the table below.

| Enzyme Concentration | $\Delta R$ |
|---|---|
| 0.01 CPU/l | 4.0 |
| 0.04 CPU/l | 6.7 |
| 0.08 CPU/l | 8.7 |
| 0.16 CPU/l | 9.7 |
| 0.50 CPU/l | 11.2 |

The differential remission values ($\Delta R$) show that the polypeptide having the amino acid sequence shown as amino acids 1 to 311 of SEQ ID NO: 2 possesses a good washability.

Example 3

Stability in Detergents

The stability of the polypeptide having the amino acid sequence shown as amino acids 1 to 311 of SEQ ID NO: 2 was tested in the presence of detergents. The detergents used in this test were an American type powder detergent and an American type liquid detergent.

The residual activity was determined after 60 minutes at 40° C. Enzyme dosage was 0.3 CPU/l.

| | Residual activity | |
|---|---|---|
| Powder detergent: | 0.9 g/l | 100% |
| Liquid detergent: | 2.0 g/l | 95% |

This experiment shows that the polypeptide having the amino acid sequence shown as amino acids 1 to 311 of SEQ ID NO: 2 is stable in detergents under wash conditions.

Example 4

Wash Performance in US liquid detergent compared to Savinase®

| Wash conditions: | |
|---|---|
| Detergent dosage: | 8 g/l |
| Wash temperature: | 30° C. |
| Wash time: | 12 minutes |
| Water hardness: | 6° dH ($Ca^{2+}:Mg^{2+}$ = 2:1) |
| pH: | Not adjusted (8.2 before wash) |
| Enzyme concentrations: | 1.25, 2.5, 5, 10, 30 nM |
| Test system: | 150 ml glass beakers with a stirring rod |
| Textile/volume: | 5 textile pieces (∅ 2.5 cm) in 50 ml detergent |
| Test material: | EMPA117 (blood, ink, milk) and CS8 (milk) |

Detergents:

The detergents used were obtained from supermarkets in the USA (Tide Mountain Spring, Deep Clean Formula 1999 P&G 40084959). Prior to use all enzymatic activity in the detergent was inactivated by microwave treatment.

Swatches:

The swatches used were EMPA117, obtained from EMPA Testmaterialen, Movenstrasse 12, CH-9015. St. Gall, Switzerland, and CS8, obtained from CFT Center For Testmaterials, Hoekerstraat 12, 3133 KR Vlaardingen, The Netherlands.

Reflectance:

Measurement of reflectance (R) on the test materials was done at 460 nm using a Macbeth ColorEye 7000 photometer. The measurements were done in accordance with the manufacturer's protocol.

Evaluation:

The evaluation of the wash performance of a protease is determined by the improvement factor of the protease investigated.

The improvement factor, $IF_{dose/response}$, is defined as the ratio between the slopes of the wash performance curves for a detergent containing the proteases to be investigated and the same detergent containing a reference protease (in this case Savinase®) at the asymptotic concentration of the protease goes to zero, i.e. $IF_{dose,response} = a/a_{ref}$.

The wash performance is calculated according to the below formula I:

$$R = R_0 + (a \cdot \Delta R_{max} \cdot c)/(\Delta R_{max} + a \cdot c) \quad (I)$$

where

R is the wash performance in reflectance units; $R_0$ is the intercept of the fitted curve with the y-axis (blind); a is the slope of the fitted curve as c→0; c is the enzyme concentration; and $\Delta R_{max}$ is the theoretical maximal wash effect as c→∞.

| | Results: | |
|---|---|---|
| Protease | Swatch | $IF_{dose/response}$ |
| Savinase ® | EMPA117 | 1 |
| SEQ ID NO:2 | EMPA117 | 4.7 |
| Savinase ® | CS8 | 1 |
| SEQ ID NO:2 | CS8 | 3.1 |

As it appears, the protease having the amino acid sequence shown as amino acids 1–311 of SEQ ID NO: 2 exhibits improved wash performance as compared to Savinase®.

Example 5

Determination of Sequence

The clone of interest was selected as protease positive from screening of a Bacillus sp. TY145 NCIMB no. 40339 gene library on agar plate with skim milk. The clone contains an approximately 4.2 Kb insert. The insert was PCR amplified using Expand Long Template PCR System (Roche) according to manufactures instruction. Transposon insertion was done directly on the PCR product using the GPS-1, Genome Priming Systems, from New England Biolabs Inc. The transposon inserted DNA pool was digested with Hind III (New England Biolabs inc.) and ligated into Hind III digested pZErO 2.0 (Invitrogen). The DNA was transformed into *E. coli* by standard procedures. Qiagen (Qiagen, USA) purified plasmid DNA from chloramphenicol and kanamycin resistant clones were isolated from *E. coli*. Inserts of the isolated clones were sequenced with M13 forward and reverse primers, PrimerS (New England Biolabs inc.) and PrimerN (New England Biolabs inc.), using the Taq deoxy terminal cycle sequencing kit (Perkin Elmer, USA) and an Applied Biosystems ABI PRISM™ 377 DNA Sequencer according to the manufacturers instructions. By combining the DNA sequences obtained by the above mention method, the DNA sequence of the original insert in PRT1313 was determined. DNA sequence analysis revealed an open reading frame, ORF, containing the DNA sequence for the Alkaline Bacillus protease TY145 (SEQ ID NO: 1).

Example 6

Expression of the apr protease from Bacillus sp. TY145 in *Bacillus subtilis*

The AprTY145 protease gene was cloned into a derivative of pSX120* (WO91/09129) and transformed to *B. subtilis* DN497 as an in frame fusion to the aprH309 signal sequence and flanked C-terminal by the terminator of aprH309.

The apr protease gene was isolated by PCR from chromosomal DNA of Bacillus sp. TY145 (NCIMP No. 40339; WO 92/17577) by the specific primers pep81 (SEQ ID NO: 3) and pep86 (SEQ ID NO: 4).

The pro-region and the coding region for the mature apr protease were fused in frame with the signal sequence of aprH309 (WO 89/06279) via a unique Cla1 site. The aprTY145 PCR sequence was inserted into the pSX222 vector as a Cla1 Mlu1 fragment replacing the original pro and mature sequence of the aprH309 protease. (the sequence of fused protease+the terminator region of aprH309 from the ATG start to BamH1 behind the aprH309 terminator is set forth in SEQ ID NO: 5)

After ligation the DNA was transformed to competent *B. subtilis* cells (DN497, delta aprE, delta nprE) and transformants resistant towards 10 microgram/ml chloramphenicol was isolated. (Transformation of *B. subtilis* was performed as described by Dubnau et al., 1971, J. Mol. Biol. 56, pp. 209–221.)

The DNA sequence obtained from the transformants confirms the insert to be the correct fusion of the aprH309 and the aprTY145 protease.

The Mw of the AprTY145 protease recovered from this transformant was analysed by mass spectoscopy and the Mw of 31784 Dalton is exactly identical to the Mw of the Apr protease obtained from the B. sp. TY145.

*) The pSX222 vector used in this experiment is a derivative of pSX120—In pSX222 the original aprH309 gene is replaced by a partially synthetic DNA sequence of the AprH309 protease. The synthetic gene has additional restriction sites integrated in the coding sequence and a shorter terminator sequence compared to the aprH309 gene in pSX120.

---

What is claimed is:

1. An isolated nucleic acid sequence encoding a polypeptide having proteolytic activity, selected from the group consisting of:
   (a) a nucleic acid sequence encoding a polypeptide having an amino acid sequence which has at least 75% identity with amino acids 1 to 311 of SEQ ID NO: 2;
   (b) a nucleic acid sequence having at least 70% identity with nucleotides 371 to 1303 of SEQ ID NO: 1;
   (c) a nucleic acid sequence, which hybridizes under low stringency conditions, wherein low stringency conditions are defined as prehybridization and hybridization at 42° C. in 5×SSPE, 0.3% SDS, 200 micrograms/ml sheared and denatured salmon sperm DNA, and 25% formamide, following standard Southern blotting procedures, with the nucleic acid sequence of SEQ ID NO: 1 or its complementary strand; and
   (d) a subsequence of (a), (b), or (c), wherein the subsequence encodes a polypeptide fragment which has proteolytic activity.

2. The nucleic acid sequence of claim 1, which encodes a polypeptide having an amino acid sequence which has at least 75% identity with amino acids 1 to 311 of SEQ ID NO: 2.

3. The nucleic acid sequence of claim 2, which encodes a polypeptide having an amino acid sequence which has at least 80% identity with amino acids 1 to 311 of SEQ ID NO: 2.

4. The nucleic acid sequence of claim 3, which encodes a polypeptide having an amino acid sequence which has at least 90% identity with amino acids 1 to 311 of SEQ ID NO: 2.

5. The nucleic acid sequence of claim 4, which encodes a polypeptide having an amino acid sequence which has at least 95% identity with amino acids 1 to 311 of SEQ ID NO: 2.

6. The nucleic acid sequence of claim 5, which encodes a polypeptide having an amino acid sequence which has at least 99% identity with amino acids 1 to 311 of SEQ ID NO: 2.

7. The nucleic acid sequence of claim 1, which encodes a polypeptide comprising the amino acids 1 to 311 of SEQ ID NO: 2.

8. The nucleic acid sequence of claim 7, which encodes a polypeptide consisting of the amino acids 1 to 311 of SEQ ID NO: 2.

9. The nucleic acid sequence of claim 1, which has at least 70% identity with nucleotides 371 to 1303 of SEQ ID NO: 1.

10. The nucleic acid sequence of claim 9, which has at least 80% identity with nucleotides 371 to 1303 of SEQ ID NO: 1.

11. The nucleic acid sequence of claim 10, which has at least 90% identity with nucleotides 371 to 1303 of SEQ ID NO: 1.

12. The nucleic acid sequence of claim 11, which has at least 95% identity with nucleotides 371 to 1303 of SEQ ID NO: 1.

13. The nucleic acid sequence of claim 12, which has at least 99% identity with nucleotides 371 to 1303 of SEQ ID NO: 1.

14. The nucleic acid sequence of claim 1, which comprises the nucleotides 371 to 1303 of SEQ ID NO: 1.

15. The nucleic acid sequence of claim 14, which consists of nucleotides 371 to 1303 of SEQ ID NO: 1.

16. The nucleic acid sequence of claim 1, wherein the nucleic acid sequence hybridizes under low stringency conditions, wherein low stringency conditions are defined as prehybridization and hybridization at 42° C. in 5×SSPE, 0.3% SDS, 200 micrograms/ml sheared and denatured salmon sperm DNA, and 25% formamide following standard Southern blotting procedures, with the nucleic acid sequence of SEQ ID NO: 1 or its complementary strand.

17. The nucleic acid sequence of claim 16, wherein the nucleic acid sequence hybridizes under medium stringency conditions, wherein medium stringency conditions are defined as prehybridization and hybridization at 42° C. in 5×SSPE, 0.3% SDS, 200 micrograms/ml sheared and denatured salmon sperm DNA, and 35% formamide, following standard Southern blotting procedures.

18. The nucleic acid sequence of claim 17, wherein the nucleic acid sequence hybridizes under high stringency conditions, wherein high stringency conditions are defined as prehybridization and hybridization at 42° C. in 5×SSPE, 0.3% SDS, 200 micrograms/ml sheared and denatured salmon sperm DNA, and 50% formamide, following standard Southern blotting procedures.

19. The nucleic acid sequence of claim 1, which encodes a polypeptide which has at least 20% of the proteolytic activity of amino acids 1 to 311 of SEQ ID NO: 2.

20. A nucleic acid construct comprising the nucleic acid sequence of claim 1 operably linked to one or more control sequences, which direct the production of the polypeptide in a suitable expression host.

21. A recombinant expression vector comprising the nucleic acid construct of claim 20 a promoter, and transcriptional and translational stop signals.

22. A recombinant host cell comprising the nucleic acid construct of claim 20.

23. The host cell of claim 22, which is a bacterium.

24. The host cell of claim 23, which is a Bacillus.

25. The host cell of claim 24, which is a *Bacillus subtilis*.

26. A method for producing a polypeptide having proteolytic activity, the method comprising (a) cultivating the host cell of claim 22 under conditions conducive to the production of the polypeptide, and (b) recovering the polypeptide.

* * * * *

SEQUENCE LISTING

```
<160> NUMBER OF SEQ ID NOS: 5

<210> SEQ ID NO 1
<211> LENGTH: 1306
<212> TYPE: DNA
<213> ORGANISM: Bacillus sp.
<220> FEATURE:
<221> NAME/KEY: CDS
<222> LOCATION: (50)..(1303)
<223> OTHER INFORMATION:
<221> NAME/KEY: mat_peptide
<222> LOCATION: (371)..()
<223> OTHER INFORMATION:

<400> SEQUENCE: 1
aaatataata ttagcgaaag agaaattaca atttgagagg agaaatggg atg aag        55
                                                       Met Lys aaa  aga aga gca ttt gca  gcc aca tta ctc agt att acg atg gga tta   103
Lys  Arg Arg Ala Phe Ala  Ala Thr Leu Leu Ser Ile Thr Met Gly Leu
-105              -100                -95                 -90 tcc gta ttt tca aca gga gca ctt gca aaa gac aaa gtt gag gta aag    151
Ser Val Phe Ser Thr Gly Ala Leu Ala Lys Asp Lys Val Glu Val Lys
             -85                -80                 -75 gaa caa gat tca tat cgt gtg cta atc aaa gca cca act aca tca atc    199
Glu Gln Asp Ser Tyr Arg Val Leu Ile Lys Ala Pro Thr Thr Ser Ile
```

```
                -70                 -65                 -60
agt act ttt caa tca caa tac gat gtc cgt tgg gat ttt ggc aaa gag          247
Ser Thr Phe Gln Ser Gln Tyr Asp Val Arg Trp Asp Phe Gly Lys Glu
        -55                 -50                 -45 gga ttt aca aca gat gtt gat gcc aaa cag ctc caa acg ctt caa agc          295
Gly Phe Thr Thr Asp Val Asp Ala Lys Gln Leu Gln Thr Leu Gln Ser
    -40                 -35                 -30 aac aaa gac att caa att cag aag gta aat gaa atg aca gta gaa act          343
Asn Lys Asp Ile Gln Ile Gln Lys Val Asn Glu Met Thr Val Glu Thr
-25                 -20                 -15                 -10 gtt aca aca gaa aag gcg gaa gtg acg gcg gta cca agt aca caa acc          391
Val Thr Thr Glu Lys Ala Glu Val Thr Ala Val Pro Ser Thr Gln Thr
                -5                  -1  1                   5 cct tgg ggc ata aag tca att tat aat gat caa tca att aca aaa aca          439
Pro Trp Gly Ile Lys Ser Ile Tyr Asn Asp Gln Ser Ile Thr Lys Thr
            10                  15                  20 act gga ggc agc gga att aag gta gct gtt tta gat aca ggg gtt tat          487
Thr Gly Gly Ser Gly Ile Lys Val Ala Val Leu Asp Thr Gly Val Tyr
        25                  30                  35 aca agc cat tta gat tta gct ggt tct gcc gag caa tgc aag gat ttt          535
Thr Ser His Leu Asp Leu Ala Gly Ser Ala Glu Gln Cys Lys Asp Phe
40                  45                  50                  55 acc caa tct aat cct tta gta gat ggt tca tgc acc gat cgc caa ggg          583
Thr Gln Ser Asn Pro Leu Val Asp Gly Ser Cys Thr Asp Arg Gln Gly
                60                  65                  70 cat ggt aca cat gtt gcc gga act gta ttg gcg cat gga ggc agt aat          631
His Gly Thr His Val Ala Gly Thr Val Leu Ala His Gly Gly Ser Asn
            75                  80                  85 gga caa ggc gtt tac ggg gtg gct ccg caa gcg aaa cta tgg gca tat          679
Gly Gln Gly Val Tyr Gly Val Ala Pro Gln Ala Lys Leu Trp Ala Tyr
        90                  95                  100 aaa gta tta gga gat aac ggc agc gga tac tct gat gat att gca gca          727
Lys Val Leu Gly Asp Asn Gly Ser Gly Tyr Ser Asp Asp Ile Ala Ala
105                 110                 115 gct atc aga cat gta gct gat gaa gct tca cgt aca ggt tcc aaa gta          775
Ala Ile Arg His Val Ala Asp Glu Ala Ser Arg Thr Gly Ser Lys Val
120                 125                 130                 135 gta att aat atg tcg cta ggt tca tct gcc aag gat tca ttg att gct          823
Val Ile Asn Met Ser Leu Gly Ser Ser Ala Lys Asp Ser Leu Ile Ala
            140                 145                 150 agt gca gta gat tat gca tat gga aaa ggt gta tta atc gtt gct gcg          871
Ser Ala Val Asp Tyr Ala Tyr Gly Lys Gly Val Leu Ile Val Ala Ala
        155                 160                 165 gct ggt aat agt ggg tca ggc agc aat aca atc ggc ttt cct ggc ggg          919
Ala Gly Asn Ser Gly Ser Gly Ser Asn Thr Ile Gly Phe Pro Gly Gly
    170                 175                 180 ctt gta aat gca gtg gca gta gcg gca ttg gag aat gtt cag caa aat          967
Leu Val Asn Ala Val Ala Val Ala Ala Leu Glu Asn Val Gln Gln Asn
185                 190                 195 gga act tat cga gta gct gat ttc tca tct aga ggg aat ccg gca act         1015
Gly Thr Tyr Arg Val Ala Asp Phe Ser Ser Arg Gly Asn Pro Ala Thr
200                 205                 210                 215 gct gga gat tat atc att caa gag cgt gat att gaa gtt tca gct ccg         1063
Ala Gly Asp Tyr Ile Ile Gln Glu Arg Asp Ile Glu Val Ser Ala Pro
            220                 225                 230 gga gca agt gta gag tct aca tgg tac act ggc ggt tat aat acg atc         1111
Gly Ala Ser Val Glu Ser Thr Trp Tyr Thr Gly Gly Tyr Asn Thr Ile
        235                 240                 245 agc ggt aca tca atg gct aca cct cat gta gct ggg tta gct gct aaa         1159
```

```
Ser Gly Thr Ser Met Ala Thr Pro His Val Ala Gly Leu Ala Ala Lys
        250                 255                 260 atc tgg tca gcg aat act tca tta agt cat agc caa ctg cgc aca gaa    1207
Ile Trp Ser Ala Asn Thr Ser Leu Ser His Ser Gln Leu Arg Thr Glu
265                 270                 275 ttg caa aat cgc gct aaa gta tat gat att aaa ggt ggt atc gga gcc    1255
Leu Gln Asn Arg Ala Lys Val Tyr Asp Ile Lys Gly Gly Ile Gly Ala
280                 285                 290                 295 gga aca ggt gac gat tat gca tca ggg ttc gga tat cca aga gta aaa    1303
Gly Thr Gly Asp Asp Tyr Ala Ser Gly Phe Gly Tyr Pro Arg Val Lys
                    300                 305                 310 taa                                                                1306
```

<210> SEQ ID NO 2
<211> LENGTH: 418
<212> TYPE: PRT
<213> ORGANISM: Bacillus sp.

<400> SEQUENCE: 2

```
Met Lys Lys Arg Arg Ala Phe Ala  Ala Thr Leu Leu Ser Ile Thr Met
        -105                -100                -95

Gly Leu Ser Val Phe Ser Thr Gly Ala Leu Ala Lys Asp Lys Val Glu
        -90                 -85                 -80

Val Lys Glu Gln Asp Ser Tyr Arg Val Leu Ile Lys Ala Pro Thr Thr
-75                 -70                 -65                 -60

Ser Ile Ser Thr Phe Gln Ser Gln Tyr Asp Val Arg Trp Asp Phe Gly
                    -55                 -50                 -45

Lys Glu Gly Phe Thr Thr Asp Val Asp Ala Lys Gln Leu Gln Thr Leu
                -40                 -35                 -30

Gln Ser Asn Lys Asp Ile Gln Ile Gln Lys Val Asn Glu Met Thr Val
            -25                 -20                 -15

Glu Thr Val Thr Thr Glu Lys Ala Glu Val Thr Ala Val Pro Ser Thr
        -10                 -5                  -1   1              5

Gln Thr Pro Trp Gly Ile Lys Ser Ile Tyr Asn Asp Gln Ser Ile Thr
                    10                  15                  20

Lys Thr Thr Gly Gly Ser Gly Ile Lys Val Ala Val Leu Asp Thr Gly
                25                  30                  35

Val Tyr Thr Ser His Leu Asp Leu Ala Gly Ser Ala Glu Gln Cys Lys
            40                  45                  50

Asp Phe Thr Gln Ser Asn Pro Leu Val Asp Gly Ser Cys Thr Asp Arg
        55                  60                  65

Gln Gly His Gly Thr His Val Ala Gly Thr Val Leu Ala His Gly Gly
70                  75                  80                  85

Ser Asn Gly Gln Gly Val Tyr Gly Val Ala Pro Gln Ala Lys Leu Trp
                90                  95                  100

Ala Tyr Lys Val Leu Gly Asp Asn Gly Ser Gly Tyr Ser Asp Asp Ile
            105                 110                 115

Ala Ala Ala Ile Arg His Val Ala Asp Glu Ala Ser Arg Thr Gly Ser
        120                 125                 130

Lys Val Val Ile Asn Met Ser Leu Gly Ser Ser Ala Lys Asp Ser Leu
    135                 140                 145

Ile Ala Ser Ala Val Asp Tyr Ala Tyr Gly Lys Gly Val Leu Ile Val
150                 155                 160                 165

Ala Ala Ala Gly Asn Ser Gly Ser Gly Ser Asn Thr Ile Gly Phe Pro
                    170                 175                 180
```

```
Gly Gly Leu Val Asn Ala Val Ala Val Ala Ala Leu Glu Asn Val Gln
            185                 190                 195

Gln Asn Gly Thr Tyr Arg Val Ala Asp Phe Ser Ser Arg Gly Asn Pro
        200                 205                 210

Ala Thr Ala Gly Asp Tyr Ile Ile Gln Glu Arg Asp Ile Glu Val Ser
215                 220                 225

Ala Pro Gly Ala Ser Val Glu Ser Thr Trp Tyr Thr Gly Gly Tyr Asn
230                 235                 240                 245

Thr Ile Ser Gly Thr Ser Met Ala Thr Pro His Val Ala Gly Leu Ala
                250                 255                 260

Ala Lys Ile Trp Ser Ala Asn Thr Ser Leu Ser His Ser Gln Leu Arg
                265                 270                 275

Thr Glu Leu Gln Asn Arg Ala Lys Val Tyr Asp Ile Lys Gly Gly Ile
            280                 285                 290

Gly Ala Gly Thr Gly Asp Asp Tyr Ala Ser Gly Phe Gly Tyr Pro Arg
        295                 300                 305

Val Lys
310
```

<210> SEQ ID NO 3
<211> LENGTH: 45
<212> TYPE: DNA
<213> ORGANISM: Artificial Sequence
<220> FEATURE:
<223> OTHER INFORMATION: Primer

<400> SEQUENCE: 3
gttcatcgat cgcatcggct gcacttgcaa aagacaaagt tgagg                    45

<210> SEQ ID NO 4
<211> LENGTH: 34
<212> TYPE: DNA
<213> ORGANISM: Artificial Sequence
<220> FEATURE:
<223> OTHER INFORMATION: Primer

<400> SEQUENCE: 4
atgcaggcgt tattttactc ttggatatcc gaac                               34

<210> SEQ ID NO 5
<211> LENGTH: 1330
<212> TYPE: DNA
<213> ORGANISM: Artificial Sequence
<220> FEATURE:
<223> OTHER INFORMATION: Synthetic

<400> SEQUENCE: 5
atgaagaaac cgttggggaa aattgtcgca agcaccgcac tactcatttc tgttgctttt    60
agttcatcga tcgcatcggc tgcacttgca aaagacaaag ttgaggtaaa ggaacaagat   120
tcatatcgtg tgctaatcaa agcaccaact acatcaatca gtactttca atcacaatac    180 gatgtccgtt gggattttgg caagaggga tttacaacag atgttgatgc caaacagctc    240
caaacgcttc aaagcaacaa agacattcaa attcagaagg taaatgaaat gacagtagaa    300
actgttacaa cagaaaaggc ggaagtgacg gcggtaccaa gtacacaaac ccctggggc    360 ataaagtcaa tttataatga tcaatcaatt acaaaaacaa ctggaggcag cggaattaag    420
gtagctgttt tagatacagg ggtttataca agccatttag atttagctgg ttctgccgag   480
caatgcaagg attttaccca atctaatcct ttagtagatg gttcatgcac cgatcgccaa   540

-continued

```
gggcatggta cacatgttgc cggaactgta ttggcgcatg gaggcagtaa tggacaaggc    600
gtttacgggg tggctccgca agcgaaacta tgggcatata aagtattagg agataacggc    660
agcggatact ctgatgatat tgcagcagct atcagacatg tagctgatga agcttcacgt    720
acaggttcca aagtagtaat taatatgtcg ctaggttcat ctgccaagga ttcattgatt    780
gctagtgcag tagattatgc atatggaaaa ggtgtattaa tcgttgctgc ggctggtaat    840
agtgggtcag gcagcaatac aatcggcttt cctggcgggc ttgtaaatgc agtggcagta    900
gcggcattgg agaatgttca gcaaaatgga acttatcgag tagctgattt ctcatctaga    960
gggaatccgg caactgctgg agattatatc attcaagagc gtgatattga agtttcagct   1020
ccgggagcaa gtgtagagtc tacatggtac actggcggtt ataatacgat cagcggtaca   1080
tcaatggcta cacctcatgt agctgggtta gctgctaaaa tctggtcagc gaatacttca   1140
ttaagtcata gccaactgcg cacagaattg caaaatcgcg ctaaagtata tgatattaaa   1200
ggtggtatcg gagccggaac aggtgacgat tatgcatcag ggttcggata tccaagagta   1260
aaataacgcg ttaatcaata aaaaaacgct gtgcggttaa agggcacagc gttttttgt    1320 gtatggatcc                                                          1330
```